United States Patent
Douglas et al.

(10) Patent No.: US 11,210,785 B1
(45) Date of Patent: Dec. 28, 2021

(54) LABELING SYSTEM FOR CROSS-SECTIONAL MEDICAL IMAGING EXAMINATIONS

(71) Applicants: Robert Edwin Douglas, Winter Park, FL (US); Kathleen Mary Douglas, Winter Park, FL (US); David Byron Douglas, Winter Park, FL (US)

(72) Inventors: Robert Edwin Douglas, Winter Park, FL (US); Kathleen Mary Douglas, Winter Park, FL (US); David Byron Douglas, Winter Park, FL (US)

( * ) Notice: Subject to any disclaimer, the term of this patent is extended or adjusted under 35 U.S.C. 154(b) by 0 days.

(21) Appl. No.: 17/228,659

(22) Filed: Apr. 12, 2021

Related U.S. Application Data

(63) Continuation-in-part of application No. 17/072,350, filed on Oct. 16, 2020, which is a continuation-in-part of application No. 16/842,631, filed on Apr. 7, 2020.

(60) Provisional application No. 62/916,262, filed on Oct. 17, 2019, provisional application No. 63/010,004, filed on Apr. 14, 2020.

(51) Int. Cl.
*G06T 7/00* (2017.01)
*G06T 7/187* (2017.01)

(52) U.S. Cl.
CPC ............ *G06T 7/0012* (2013.01); *G06T 7/187* (2017.01); *G06T 2207/10081* (2013.01); *G06T 2207/10088* (2013.01); *G06T 2207/10104* (2013.01); *G06T 2207/10108* (2013.01); *G06T 2207/20081* (2013.01); *G06T 2207/20084* (2013.01); *G06T 2207/30096* (2013.01)

(58) Field of Classification Search
CPC ............. G06K 2209/05; G06K 9/6254; G06K 9/6262; G06K 9/6267; G16H 30/20
See application file for complete search history.

(56) References Cited

U.S. PATENT DOCUMENTS

2020/0286614 A1\* 9/2020 Do .......................... G16H 15/00

\* cited by examiner

*Primary Examiner* — Ross Varndell

(57) ABSTRACT

This patent includes a method for displaying a reference image to the radiologist similar to the current image the radiologist is actively reviewing. Additionally, this patent provides a method to enhance both an educational experience and an image analysis process for an imaging examination by incorporating classification of anatomic features and methods to teach a user the names of imaging findings.

19 Claims, 15 Drawing Sheets

PRIOR ART

SMART IMAGE CONSULTING PROCESS

LIST OF FACTORS INDICATING THAT A FIRST USER NEEDS HELP WITH IMAGE CLASSIFICATION

| List of factors of a first user needing help |
|---|
| • Help button<br>• Facial recognition<br>• Eye tracking<br>• Difference in opinion from radiologist and AI per RAML<br>• Consulting request (e.g., arrow(s), 3D cursor(s)) |

Figure 4

MULTI-MARK UP, MULTI-CONSULTANT PROCESS AND AN EXAMPLE

MULTI-USER IMAGE ANALYSIS AND REPORTING

EXAMPLES OF IMAGE VIEWING STRATEGIES DURING THE MULTI-MARK UP, MULTI-CONSULTANT PROCESS

Viewing strategies

- Conventional viewing strategies (e.g., modifying the visual representation, such as changing the color and tranparency, filtering, etc.)
- Advanced viewing strategies (e.g., US Patent 10,586,400, PROCESSING 3D MEDICAL IMAGES TO ENHANCE VISUALIZATION)
- Interaction of 3D dataset with geo-registered tools, as described in US Patent 10,712,837, USING GEO-REGISTERED TOOLS TO MANIPULATE THREE-DIMENSIONAL MEDICAL IMAGES
- Interaction of 3D dataset with virtual tools, as described in PCT/US19/47891, A VIRTUAL TOOL KIT FOR 3D IMAGING
- "Ghost imaging" per US Patent Application 16/010,925, INTERACTIVE PLACEMENT OF A 3D DIGITAL REPRESENTATION OF A SURGICAL DEVICE OR ANATOMIC FEATURE INTO A 3D RADIOLOGIC IMAGE FOR PRE-OPERATIVE PLANNING
- Flow visualization features, as described in US Patent Applications 16/506,073, A METHOD FOR ILLUSTRATING DIRECTION OF BLOOD FLOW VIA POINTERS, and 16/779,658, 3D IMAGING OF VIRTUAL FLUIDS AND VIRTUAL SOUNDS
- Voxel manipulation strategies, per US Patent Application 16/195,251, INTERACTIVE VOXEL MANIPULATION IN VOLUMETRIC MEDICAL IMAGING FOR VIRTUAL MOTION, DEFORMABLE TISSUE, AND VIRTUAL RADIOLOGICAL DISSECTION

Figure 9

ALGORITHM THAT FINDS THE MOST APPROPRIATE CONSULT
- Not disturb others from work
- Analyze past reports of each user in the group
- Analyze past images of each user in the group
- Analyze past consult patterns
- Analyze feedback from past consult patterns (e.g., satisfaction scores)
- Urgency of the case
- Option to exclude user(s)
- See which user(s) are available

Radiologist #456
General radiologist with special skill of asbestos related lung disease
*Needs help with temporal bone
1100

Fig. 11B

Radiologist #911
Neuroradiologist with specialty skills of cerebral vasculitis
1101

Radiologist #415
Neuroradiologist with specialty skills of phakomatoses
1104

Radiologist #316
Neuroradiologist with specialty skills of PET imaging of dementia
1102

Radiologist #899
Neuroradiologist with specialty skills of temporal bone lesions
1105

Radiologist #200
Neuroradiologist with specialty skills of skull base tumors
1103

Fig. 11C

Radiologist #322
Musculoskeletal radiologist with special skill of metabolic bone disease
*Connects Radiologist 456 with 899
1106

RVU MODIFIED BASED ON IMAGE DIFFICULTY

- Imaging finding
    - Presence of athology
- Patient history (e.g., indication of study)
- Patient labs (e.g., WBC of 20)
- Urgency of exaimation
- Consulting process

Figure 12

| Unread Examinations | General (open to anyone) cases needing consultation | Specific (only seen by you) cases needing consultation |
|---|---|---|
| - | - | - |
| - | - | - |
| - | - | - |
| - | - | - |
| - | - | - |
| - | - | - |
| - | - | - |
| - | - | - |

Figure 13

USING AI TO DETERMINE AN OPTIMUM REFERENCE IMAGE

Determine structure(s) of interest or area of interest in a first imaging examination (e.g., a patient's cross-sectional medical imaging examination comprises at least one of a computed tomography (CT) scan, a magnetic resonance imaging (MRI) examination, a positron emission tomography (PET) scan, a single photon emission computed tomography (SPECT) scan and an ultrasound examination).
Option to:
• perform segmentation to delineate the boundary of the structure of interest.
1400

Analyze (using artificial intelligence) a database of images to determine a second imaging examination from a database of imaging examinations (e.g., archive of labeled imaging datasets, archive of unlabeled imaging datasets) which is a close (or closest) match to the structure of interest or area of interest in the first imaging examination.
1401

Presenting the close (or closest) match to a user.
Presentation options include:
• present the image from the equivalent volume rendered appearance (cause a volume rendered image of the second imaging examination to match the first imaging examination)
• present the image from the equivalent slice (cause the second imaging examination to be reconstructed to match the first imaging examination)
• present the image using the same grayscale appearance (cause the second imaging examination to have the same window width and window level setting to match the first imaging examination)
• Note that in some embodiments, the current imaging examination can undergo image processing to match the appearance of the reference image(s).
Analysis options include:
• user review of a report from the second image to see what the past radiologist said about the structure of interest / area of interest
• perform smart image consult process
1402

Figure 14

USING AI TO PERFORM ANATOMIC LABELING OF A PATIENT'S EXAMINATION

Determine (user selects) an unlabeled structure of interest (e.g., large blood vessel in the abdomen) for an image (e.g., slice, volume rendered image) for a patient 1500

↓

Analyze (using artificial intelligence) a database of images (wherein the images are labeled) to determine a classification of the structure of interest (e.g., "aorta") for the structure of interest 1501

↓

Generate a label (e.g., "aorta") to correspond to said classification. Deliver said label for said structure of interest via visual text notification. Note that the structure can be an anatomic finding or a pathologic finding or a device (medical device or surgical device or an artifact).
1502

↓

Present a location indicator to communicate to a user the precise spot of the label on the image comprising:
- Digital object (e.g., red dot) presented at the finding (anatomic or pathologic finding) on the image to correspond to the label
- Mouse hovers over structure of interest and the label is displayed on a screen
- Line connects structure of interest to label
- Option to delineate the boundary of said structure of interest with a visual marker (or use other visual representation techniques taught in the patents incorporated by reference)
1503

↓

Option retrain the AI algorithm by:
- a user adjusts the location indicator
- a user adjusts the segmentation algorithm (e.g., delineation of the structure is re-defined)
1504

Figure 15

LABELING SYSTEM FOR CROSS-SECTIONAL MEDICAL IMAGING EXAMINATIONS

CROSS REFERENCE TO RELATED APPLICATIONS

This application is a continuation in part of U.S. patent application Ser. No. 17/072,350 filed on Oct. 16, 2020, which is a continuation in part of U.S. patent application Ser. No. 16/842,631 filed on Apr. 7, 2020, which claims the benefit of U.S. Provisional 62/916,262 filed on Oct. 17, 2019. This application also claims the benefit of U.S. Provisional 63/010,004 filed on Apr. 14, 2020.

TECHNICAL FIELD

Aspects of this disclosure are generally related to image analysis.

INTRODUCTION

There are multiple subspecialties within the field of radiology. For example, the subspecialties include: neuroradiology; nuclear medicine; musculoskeletal radiology; cardiac radiology; and mammography. An imaging examination such as a CT scan of the chest, abdomen and pelvis can contain multiple abnormalities. For example, there could be an abnormality of the spine, which would best be evaluated by a neuroradiologist and an abnormality of the liver, which would best be evaluated by an abdominal imaging radiologist.

SUMMARY

All examples, aspects and features mentioned in this document can be combined in any technically conceivable way.

First, we will explain the problem that this patent overcomes. You have an image. You have a finding. You don't know what the finding is? How to classify it? You don't know who can solve it. How to find the right person? In this patent, a solution to the above problem is provided. In a broad sense, a general and specific user pool is created, along with a point system for the reward.

Further, this patent improves on PCT/US2019/023968, RADIOLOGIST ASSISTED MACHINE LEARNING, filed on Mar. 26, 2019 because this patent provides an optimal consultation strategy. In Patent Application PCT/US2019/023968, RADIOLOGIST ASSISTED MACHINE LEARNING, filed on 26 Mar. 2019, a process wherein radiologists would work in a more collaborative environment was described. More specifically, a CT scan of the abdomen could be divided up into multiple different sub-volumes. Then, each sub-volume analyzed and passed to different virtual buckets. Some situations where there was a difference in opinion from the artificial intelligence system and the radiologist were also described. In these situations, a process of passing the volume to another radiologist for a second opinion could be performed. Options included are manual consultation process and using computer algorithms (e.g., AI) to perform the consultations. For example, an artificial intelligence system can perform predictions on who to send the images to based on age, gender, type of scan, and feedback from past consultation patterns. Thus, this patent improves on the current process for image analysis by developing a smart peer-to-peer consulting process. This patent application improves on the prior art by improving the workflow and is therefore useful.

In accordance with an aspect, the preferred method comprises a method comprising: reviewing, by a first user, an image; selecting a second user from a group of users wherein the second user is qualified to classify the image; upon an input from the first user, presenting the image to the second user; reviewing, by the second user, the image; and presenting the second user's classification of the image to the first user.

Some embodiments comprise sending the image into a bin where the group of users can view the image.

Some embodiments comprise wherein the second user performs selection of the second user. Some embodiments comprise wherein a third user performs selection of the second user.

Some embodiments comprise wherein a set of characteristics is used to select the second user. The set of characteristics may include prior image classifications, prior images and feedback from past consult patterns wherein feedback comprises the first reviewer rating the quality of the second user's classification. In addition, the set of characteristics includes an availability of each user in the group. In addition, the set of characteristics includes an urgency of the image.

Some embodiments comprise wherein the second user is selected by an artificial intelligence algorithm.

Some embodiments comprise wherein, before presenting the image to the second user, the first user performs at least one of the group comprising: image processing; annotations on the image; and, selecting a portion of the image for analysis. Some embodiments comprise wherein, before presenting the classification to the first user, the second user performs at least one of the group comprising: image processing; annotations on the image; selecting a portion of the image for analysis; and, presentation of the image to at least one additional user.

Some embodiments comprise wherein the second user performs a teaching session to the first user wherein the teaching session comprises at least one of the group of: image processing; and, image annotation.

Some embodiments comprise wherein the selecting a second user occurs based on an input from the first user wherein the input consists of at least one of the group of: activating, by the first user, a help button; activating, by the first user, a consult request; detecting, by a camera, that the first user has a predetermined facial expression; detecting, by a camera, that the first user has a predetermined eye pattern; detecting, by a camera, that the first user has a predetermined combination of facial expression and eye pattern; and detecting, by a computer algorithm, that there is a difference between the first user's classification and a classification by an artificial intelligence algorithm.

Some embodiments comprise a reward system to at least one of the group comprising: the first user; the second user; and, an additional user.

Some embodiments comprise generating a modified relative value unit (RVU) of an imaging examination based on the presence of at least one imaging finding in the imaging examination.

Some embodiments comprise a modified relative value unit (RVU) of an imaging examination based on at least one of the group consisting of: indication of the study; laboratory data; consultations; and, urgency of the study.

Some embodiments comprise the classification accuracy of users in the group is determined.

Some embodiments comprise wherein a report indicates image consult.

The purpose of this patent is to also to provide an improved method of viewing and reporting on medical images. With respect to reviewing images, the method presents images to a user at a user controlled image.

In some embodiments, a medical image is a two-dimensional (2D) 'slice' which contains pixels of various shades of gray that correspond to a particular small volume within a patient's anatomy.

Prior to radiologist review, the images of the patient of interest are compared to two groupings:

Group #1 is a set of labeled images for normal patients which would include but, not be limited to categories such as: male and female; persons of differing ages (e.g., pediatric, young persons (age 6-16), young adults; middle age, older adults and elderly); persons of differing weights and sizes; different body parts. Images from this groups would encompass parts of the entire body.

Group #2 is a very large set of images (e.g., many hundreds of thousands to perhaps in the millions). These images would not be labeled and would span not only normal persons but, also persons with a wide array of maladies to include: tumors and lesions in various stages, aneurysms, fractures, blood clots, clogged arteries, other). These would also include but, not be limited to male and female persons of differing ages (e.g., pediatric, young persons (age 6-16), young adults; middle age, older adults and elderly); persons of differing weights and sizes. Images from this groups would encompass parts of the entire body. Although the body parts within the image would not have a label, there would be key words (phrases) to "normal", if that were the case and the specific malady(s) should that be the case. In the case of cancers, stage of cancer would be included.

In performing this comparison two images would be selected for each of the images in the patient's image set: one from the labeled group #1 labeled set and one from the group #2 non-labeled set of images. The objective is to obtain the closest match between each of the patient's images and/or those images from group #1 and group #2. The patient's images plus those of group #1 and group #2 would be processed and available to the radiologist when he/she began their review.

In order to perform this comparison, the image set of the patient's images must be aligned with those of the respective image sets of group #1 and group #2. By aligned, a particular spot on the patient's anatomy must coincide with that same exact spot on the group #1 and group #2 images irrespective of image number. For example, in the patient image, this particular spot might be on image #23 whereas, on group #1 patient might occur on image number #93 it might be image #46 and for group #2 patient 724,865 it might be image #14. Further, because of size differences between the current patient, and those of group #1 and group #2, multiple such particular spots must be found on the patient's image set such the selected spots generally encase the volume of interest. Given these patient's spots, interpolation can be performed to obtain a close approximation of the patient's image at hand with respect to corresponding ones in group #1 and group #2. In some embodiments, a smart localization system as taught in U.S. patent application Ser. No. 17/100,902 filed on Nov. 22, 2020, which is incorporated by reference in its entirety, can be implemented. There may also be differences based on slight rotations of the various bodies in the image sets of group #1 and group #2 with respect to the patient's image set to be corrected. Another potential difference is the level of resolution in the imaging equipment which must also be addressed. Specifically, it is the intent of this patent to cause the visual appearance of the presentation of the reference image to be as close as possible to the image under analysis. One option is to present the image from the equivalent volume rendered appearance. This can be accomplished by causing a volume rendered image of the reference imaging examination to match the imaging examination under review. Another option is to present the image from the equivalent slice. This can be accomplished by causing the reference imaging examination to be reconstructed to match the imaging examination under review. Another option is to present the image using the same grayscale appearance. This can be accomplished by causing the second imaging examination to have the same window width and window level setting to match the first imaging examination.

The following are illustrative steps in how this could be accomplished. First, set up categories which would include but, not be limited to: gender and age group; type of medical imaging equipment; body part(s) being imaged; height and weight of patient imaged, other. Use these categories to provide a more efficient computational task. The computational task would nominally be performed via the cloud since it would not be performed in emergency patient conditions or in surgical operations. Second, during the pre-radiologist preparations, a distribution of Hounsfield units would be obtained. Artificial intelligence (AI) techniques such as but, not limited to: K-means, along with standard statistical measures such as mean and standard deviation would be applied to each patient image. Note that these measures could be pre-applied the images of group #1 and group #2 to store for future computational tasks.

Determine specific spots or 'landmarks' in the patient's image sets. For example, if the head were general body part being imaged, eye sockets, ear sockets, left and right wisdom teeth are candidate landmarks. Comparable 'landmarks' would also be identified on group #1 and group #2 images. Next, given alignment of the image sets of the patient's image set with respect to those of group #1 and group #2, artificial neural networks (ANN) can be applied to find the closest match for images of group #1 and group #2 with those of the patient. Data from application of AI techniques and statistical measures would be available for use in conjunction with applying traditional pattern analysis for optimum image matching.

During the course of the radiologist review, he/she would have the opportunity to do the following: When, at any arbitrary image N within patient's image set, the radiologist could call up the corresponding image from the group #1 set of images (i.e., labeled images) and display it along side of the currently viewed patient's image. At this juncture, the radiologist could take advantage of options such as but, not limited to the following: If there were useful anatomy terminology, this terminology could be highlighted and imported/transferred into the report. For points in the patient's image for which the radiologist has a question, the radiologist could place a cursor on the pixel/area in question and a corresponding image pixel on the group #1 image would be highlighted in a manner such as but, not limited to: pointed to by arrow, encircled by a circle; changed in size and contrast. The medical terminology of this corresponding point would also be displayed. If there were questions such as but, not limited to: some bodily function, medical standards for determining normalcy, typical maladies) these could be retrieved via mechanisms such as a pull-down menu, verbal command, etc. By clicking on the pull down menu, information would be displayed for the radiologist.

Retrieve a 3D image of any radiologist selected body part and view it in 3D. This 3D image could inter alia be rotated, zoomed in on, illustrated with connections (e.g., vascular). (Note: in order for the radiologist to view the body part in 3D, some form of 3D head display unit would be needed and different left and right eye displays would need to be generated.) A visual inter relationship of the body part with other body parts could include but, not be limited to: an exploded view could be shown to provide a view how the selected body part fits with surrounding body parts; a flow of bodily fluids into/out of the body part could be illustrated; a flow of the nervous system could be illustrated; as with the 2D image, terminology relevant to the medical report could be highlighted and imported into the report. Also, pull down menus would be available for information. For any portion of body part contained in the patient's image, a boundary surrounding that part could be shown on the patient's image, itself. This will assist the radiologist discern where one type of part stops and another part begins within the image.

When, at any arbitrary image N within patient's image set, the radiologist could call up the corresponding image from the group #2 set of images (i.e., non-labeled images) and display it along side of the currently viewed image. At this juncture, the radiologist could take advantage of options such as but, not limited to the following: Review the finding, if any, concerning the group #2 image. Depending on the nature of the findings, the radiologist could: If the findings were normal, the radiologist could gain confidence in a reporting a normal condition. If the findings reported some form of malady, the radiologist could carefully inspect the patient's image for the same malady. If there were questions regarding the group #2 malady such as but, not limited to: key discriminating signs of the malady, medical standards for determining normalcy, staging criteria, possible compounding conditions (e.g., where cancer might next spread) these could be retrieved via mechanisms such as a pull-down menu, verbal command, etc. The radiologist could retrieve any arbitrary image from group #2 via the key word search.

When, at any arbitrary image N within patient's image set, the radiologist could call up the corresponding image from the group #1 set of images (i.e., labeled images) and display it. Likewise, for this same arbitrary image N within patient's image set, the radiologist could call up the corresponding image from the group #2 set of images (i.e., non-labeled images) and display it. The radiologist would have the option of displaying in a side by side manner the images from group #1 and group #2 or, displaying the three images simultaneously i.e., the patient's; group #1 image and group #2 image. At this juncture, the radiologist could select from options which include but, are not limited to: Any of the images of the patient's; group #1 and group #2 could be subtracted digitally from the other image(s). This would be particularly useful if a malady such as a tumor were present in the group #2 image and, subsequently, when group #1 image was subtracted form it (i.e., the tumor would stand out as 'not normal'). The radiologist would be alerted to a discernable potential tumor in the patient's image and he/she would have an idea where to look.

In some embodiments, a medical image is a three-dimensional (3D) volume which contains voxels of various shades of gray that correspond to a particular small volume within a patient's anatomy. This embodiment would rely on the images of group #1 and group #2, as discussed above. (Note: in order for the radiologist to view the body part in 3D, some form of 3D head display unit would be needed and different left and right eye displays would need to be generated.) Prior to radiologist review, each of the these three sets of images would be converted to 3D using the process outlined in U.S. Pat. No. 8,384,771, which is incorporated by reference in its entirety.

Next, segment the volumes of all three image sets in accordance with a standard radiologist checklist and the type of medical imaging performed on the patient. The result of this segmentation process will include a standard set of body parts which could include but, are not limited to: organs, head, skeletal parts, limbs, etc. depending on the category of medical imaging performed on the patient at hand. A filtering process could be applied so that each body part in the patient's image set is stand alone and can be retrieved and displayed in 3D either individually in multiple parts or collectively. Note that in the 2D portion of this patent, artificial intelligence techniques and procedures were applied to individual images. Under the 3D aspects, these same procedures could be applied but, of course, these would be representative of the multiple slices that were the basis for construction of the 3D volume.

Provide labeling for the 3D volumes in group #1. External surfaces/voxels of different organs could be color coded. External surfaces/voxels of different organs could be transparent to view the internal structure; tissue types could have a variable degree of transparency and or/be color coded. A 'fly through' to see the internal structure as view point approaches the structure and then the structure disappears as the view point passes the structure. Labeling for the structures could be provided as the view point neared the structure and subsequently disappear. The labeling aspects would have the same techniques, as described for the 2D images (i.e., highlighting text for the report; pull down menus for additional information.

The radiologist could retrieve the relevant group #1 volume(s) and view either sequentially back and forth or in a side by side mode. If there were useful anatomy terminology, this terminology could be highlighted and imported/transferred into the report. For areas of the volume in question on a patient's image, the radiologist could place a cursor on the area in question and a corresponding image voxel on the group #1 image highlighted in a manner such as but, not limited to: pointed to by arrow, encircled by a sphere; changed in size and contrast. The name of this corresponding point would be displayed. If there were questions such as but, not limited to: some bodily function, medical standards for determining normalcy, typical maladies) these could be retrieved via mechanisms such as a pull-down menu, verbal command, etc.

The radiologist could retrieve the relevant group #2 volume(s) and view these volumes either sequentially back and forth or in a side by side mode. If there were useful anatomy terminology, this terminology could be highlighted and imported/transferred into the report. For areas of the volume in question on a patient's image, the radiologist could place a cursor on the area in question and a corresponding image voxel on the group #1 image highlighted in a manner such as but, not limited to: pointed to by arrow, encircled by a sphere; changed in size and contrast. The name of this corresponding voxel would be displayed. If there were questions such as but, not limited to: some bodily function, medical standards for determining normalcy, typical maladies) these could be retrieved via mechanisms such as a pull-down menu, verbal command, etc.

Some of the techniques in this patent are performed in conjunction with techniques disclosed in the following patents (all of which are incorporated by reference in their entirety): U.S. patent application Ser. No. 15/878,463, Interactive 3D cursor for use in medical imaging; U.S. patent application Ser. No. 16/010,925, Interactive placement of a 3D digital representation of a surgical device or anatomic feature into a 3D radiologic image for pre-operative planning; U.S. patent application Ser. No. 15/904,092, Processing 3D medical images to enhance visualization; U.S. patent application Ser. No. 15/949,202, Smart operating room equipped with smart surgical devices; U.S. Pat. No. 9,473,766, Method and apparatus for three dimensional viewing of images; U.S. Pat. No. 9,615,806, Method and apparatus for creation and display of artifact corrected three dimensional (3D) volumetric data from biplane fluoroscopic image acquisition; U.S. patent Ser. No. 14/644,489, Method and apparatus for creation and display of artifact corrected three dimensional (3D) volumetric data from biplane fluoroscopic image acquisition; U.S. Pat. No. 9,980,691, Method and apparatus for three dimensional viewing of images; U.S. Pat. No. 9,349,183, Method and apparatus for three dimensional viewing of images; U.S. patent application Ser. No. 16/195,251, Interactive voxel manipulation in volumetric medical imaging for virtual motion, deformable tissue, and virtual radiological dissection; U.S. patent application Ser. No. 16/509,592, Implantable markers to aid surgical operations; U.S. patent application Ser. No. 16/524,275, Using geo-registered tools to manipulate three-dimensional medical images; PCT/US19/478, A virtual tool kit for radiologists; U.S. patent application Ser. No. 16/563,985, A method and apparatus for the interaction of virtual tools and geo-registered tools; U.S. patent application Ser. No. 16/594,139, Method and apparatus for performing 3D imaging examinations of a structure under different configurations and analyzing morphologic changes; U.S. patent application Ser. No. 16/683,256, Method and apparatus for performing 3D imaging examinations of a structure under different configurations and analyzing morphologic changes; U.S. patent application Ser. No. 16/703,629, Radiologist-assisted machine learning with volume-subtending 3D cursor; PCT/US19/239, Radiologist-assisted machine learning with interactive, volume-subtending 3D cursor; U.S. provisional application No. 62/843,612, A method of creating a computer-generated patient specific image; U.S. provisional application No. 62/846,770, A method of prioritized volume rendering to improve visualization of prioritized items within a 3D volume; U.S. provisional application No. 62/850,002, A method of creating an artificial intelligence generated differential diagnosis and management recommendation tool boxes during medical personnel analysis and reporting; U.S. patent application Ser. No. 16/654,047, A method to modify imaging protocols in real time through implementation of artificial intelligence; U.S. provisional application #62/856,185, A method of image manipulation based on eye tracking; U.S. patent application Ser. No. 16/506,073, A method for illustrating direction of blood flow via pointers; U.S. patent application No. 62/906,125, A method and apparatus for stereoscopic rendering of mobile fluids; and, U.S. patent application No. 62/939,685, Method and apparatus for development of an organ-specific coordinate system.

BRIEF DESCRIPTION OF THE FIGURES

FIG. 4 illustrates an example table illustrating a list of factors indicative of a first user needing help.
FIG. 9 illustrates examples of image viewing strategies during the multi-mark up, multi-consultant process.
FIG. 10 illustrates criteria that an algorithm can use to find the most appropriate consult.
FIG. 11A illustrates features of a first user who needs help with a neuroradiology imaging examination.
FIG. 11B illustrates features of a five users who have expertise in neuroradiology.
FIG. 11C illustrates the connection of the first user with the optimum consultant.
FIG. 12 illustrates a modified relative value unit (RVU) system based on factors other than just type of imaging examination.
FIG. 13 illustrates a worklist for radiologists.
FIG. 14 illustrates using artificial intelligence to determine an optimum reference image.
FIG. 15 illustrates using artificial intelligence to perform anatomic labeling of a patient's examination.

DETAILED DESCRIPTIONS

The flow diagrams do not depict the syntax of any particular programming language. Rather, the flow diagrams illustrate the functional information one of ordinary skill in the art requires to fabricate circuits or to generate computer software to perform the processing required in accordance with the present invention. It should be noted that many routine program elements, such as initialization of loops and variables and the use of temporary variables, are not shown. It will be appreciated by those of ordinary skill in the art that unless otherwise indicated herein, the particular sequence of steps described is illustrative only and can be varied without departing from the spirit of the invention. Thus, unless otherwise stated the steps described below are unordered meaning that, when possible, the steps can be performed in any convenient or desirable order.

Figure 1:
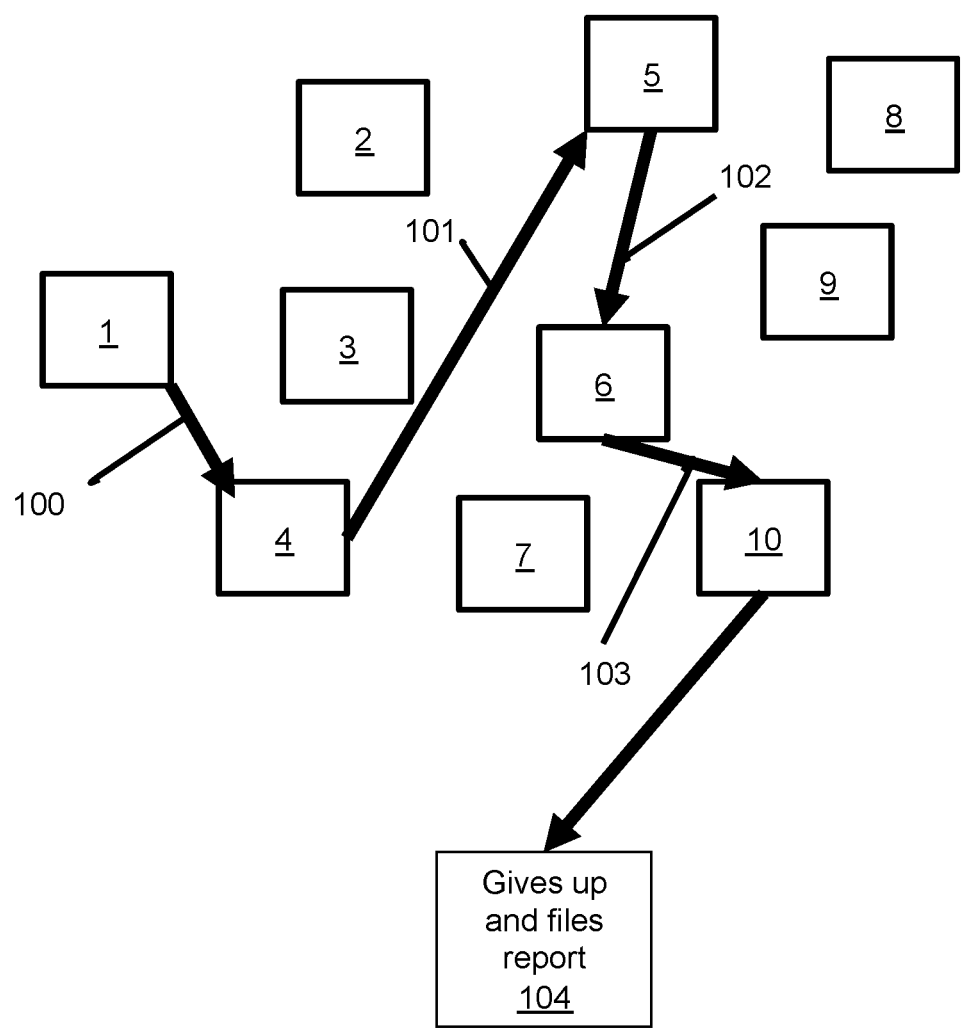
FIG. 1 illustrates the current image consulting process.

FIG. 1 illustrates the current image consulting process. 1 illustrates a radiologist, who is currently examining an image and has a question (e.g., he/she does not know how to interpret an imaging finding). 2, 3, 4, 5, 6, 7, 8 and 10 illustrates radiologists who also do know not know how to interpret the imaging examination. 9 illustrates a radiologist who confidently knows exactly how to answer the question that radiologist 1 has. Note that radiologist 1 communicated 100 (e.g., by phone, text message pop up, or walking over to the station) to radiologist 4. After reviewing the images, radiologist 4 did not know the answer. Radiologist 1 then communicated 101 over to radiologist 5. After reviewing the images, radiologist 5 did not know the answer. Radiologist 1 then communicated 102 over to radiologist 6. After reviewing the images, radiologist 6 did not know the answer. Radiologist 1 then communicated 103 over to radiologist 10. After reviewing the images, radiologist 10 did not know the answer. At this juncture, radiologist 1 has made 4 attempts.

All of which are unsuccessful since radiologists 4, 5, 6 and 10 did not know the answer. Radiologist then proceeded to give up and file the file the report 104. Note that in this scenario, radiologists 2, 3, 7, 8 and 9 were never asked. Note that radiologist 9 knew the answer, but was never asked. This illustration is important because the optimum consultant (radiologist 9) was not identified.

Figure 2:
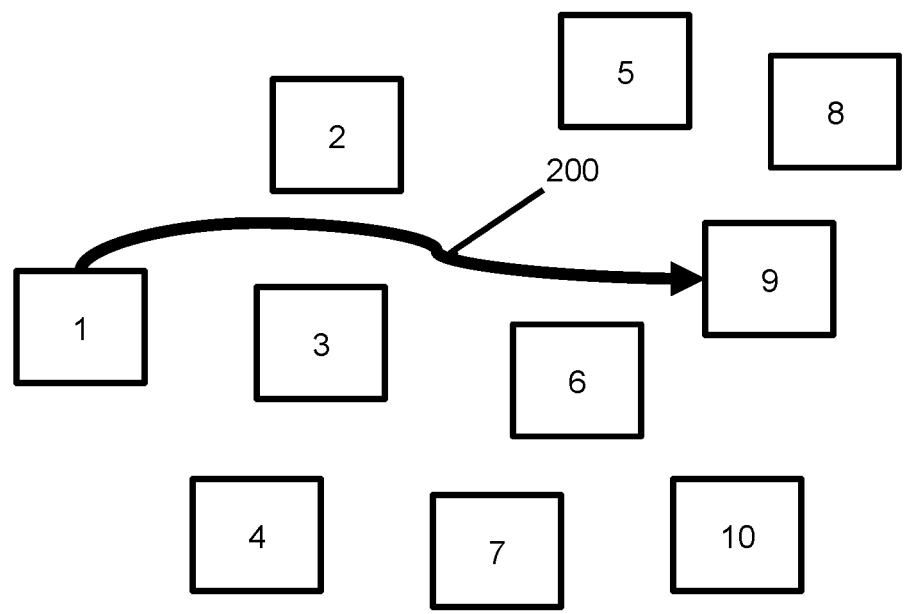
FIG. 2 illustrates the current image consulting process.

FIG. 2 illustrates the current image consulting process. 1 illustrates a radiologist, who is currently examining an image and has a question (e.g., he/she does not know how to interpret an imaging finding). Radiologist 1 implements the smart consult process described in this patent and the image is passed 200 to radiologist 9 who knowns the imaging finding confidently. 2, 3, 4, 5, 6, 7, 8 and 10 illustrates radiologists who also do not know how to interpret the imaging examination and were not consulted.

Figure 3:
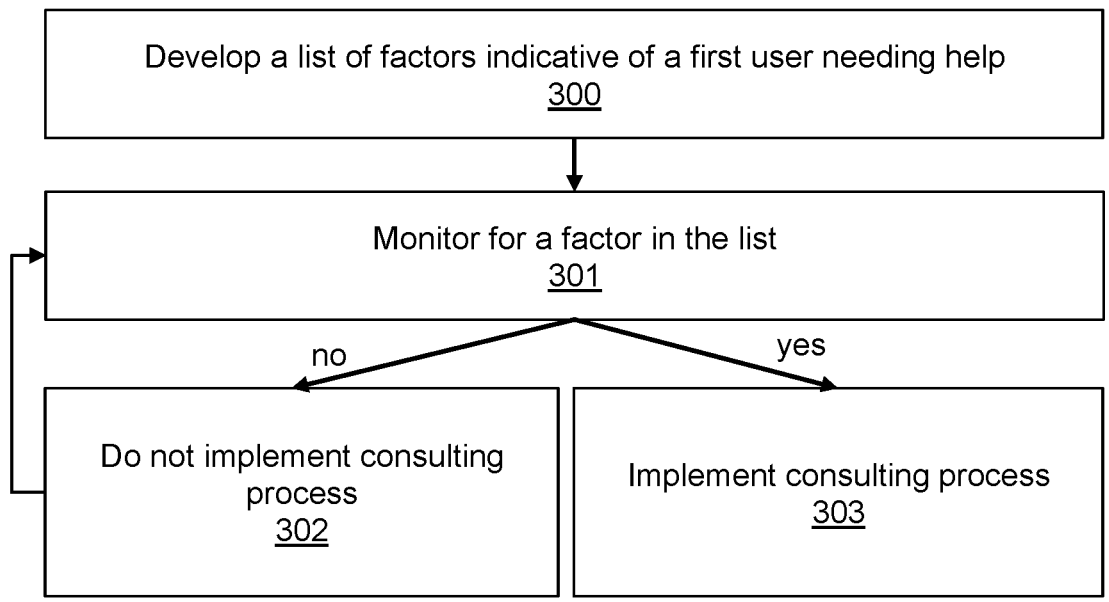
FIG. 3 illustrates when to implement the consulting process.

FIG. 3 illustrates when to implement the consulting process. 300 illustrates a processing block of developing a list of factors indicative of a first user needing help with an image. 301 illustrates a processing block of monitoring for a factor in the list. 302 illustrates a processing block which occurs when no factor is identified and wherein the consulting process is not implemented and wherein processing block 301 of monitoring for a factor in the list continues. 303 illustrates a processing block of implementing the consulting process, which is described subsequently in this patent.

FIG. 4 illustrates an example table illustrating a list of factors indicative of a first user needing help. There are several options. First, the first user could have a "help" button on their display or a help setting on their computer, which could be turned on or off. This is useful because if the first user does not want to receive help (e.g., dictating routine chest x-rays and is comfortable with all of the imaging findings and interpretation thereof), the help button turned off would (1) prevent unnecessary work from the second user and the third user and (2) prevent any pop ups offering help from the third user, which could distract the first user. Second, a camera can be utilized for real time facial expression recognition of the user who is performing the image analysis. For example, if the facial expression recognition determines that the user is confused, this can be an indicator that the first user needs help. Third, a camera can be utilized for eye tracking of the user who is performing the analysis. If the eye pattern looks too long at a particular imaging finding, then a trigger can be set for the first user needing help, as described in U.S. patent application Ser. No. 16/842,631, A SMART SCROLLING SYSTEM, which is incorporated by reference in its entirety. In some embodiments, eye tracking metrics and facial expressions can be used together to determine whether a user needs help. Fourth, the difference in opinion from a radiologist and AI algorithm can be utilized to determine whether a user needs help. This process is disclosed in PCT/US2019/023968, RADIOLOGIST ASSISTED MACHINE LEARNING, which is incorporated by reference in its entirety. Fifth, a consulting request can be performed via computer commands, such as placing an arrow or placing a 3D cursor, such as is U.S. Pat. No. 10,795,457, INTERACTIVE 3D CURSOR, which is incorporated by reference in its entirety.

Figure 5:
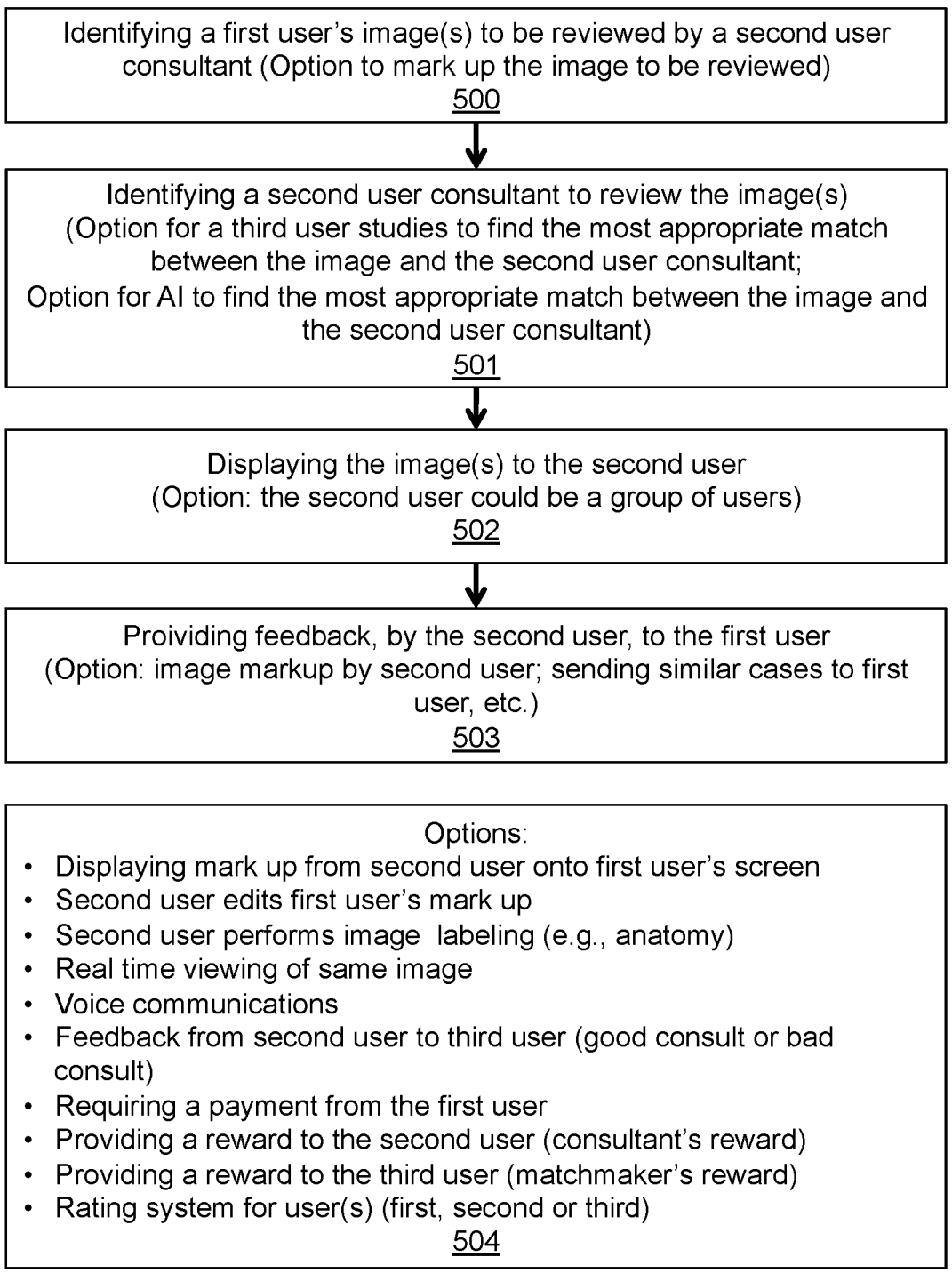
FIG. 5 illustrates implementing the smart image consulting process.

FIG. 5 illustrates implementing the smart image consulting process. 500 illustrates a processing block of identifying image(s) to be reviewed by a second user consultant. Note that there is an option to mark up the image to be reviewed. 501 illustrates a processing block of identifying a second user consultant to review the image(s). Note that there is an option for a third user studies to find the most appropriate match between the image and the second user consultant. Note that there is also an option for an artificial intelligence (AI) algorithm to find the most appropriate match between the image and the second user consultant. 502 illustrates a processing block of displaying the image(s) to the second user. Note that there is an option for the second user could be a group of users. 503 illustrates a processing block of providing feedback, by the second user, to the first user. Note that there is an option for image markup by second user. Additional feedback from a sending similar cases to first user for training purposes. There are some options. For example, a markup from second user can be displayed onto the first user's screen. A second user edits first user's mark up. A second user performs image labeling (e.g., anatomy). There can be real time viewing of same image (first user watches as second user views image by scrolling, windowing and leveling, etc.). A Voice communication can be implemented to connect the first user and the second user. Feedback from second user to third user (good consult or bad consult) can be performed. A payment (e.g., fraction of RVU from the study paid) from the first user can be utilized. A reward (e.g., fraction of RVU from the study earned) to the second user (consultant's reward) can be provided. A reward to the third user (matchmaker's reward) can be provided. A rating system for user(s) (first, second or third) can be utilized. Some radiologists could therefore earn a portion of their RVUs and even their entire RVUs through consulting work. Some radiologists could therefore earn a portion of their RVUs and even their entire RVUs through "third user" work. For example, a third user could be very good at knowing who to send images to. Feedback from second user to third user (good consult or bad consult) can be used for assessment of third user performance.

Figure 6:
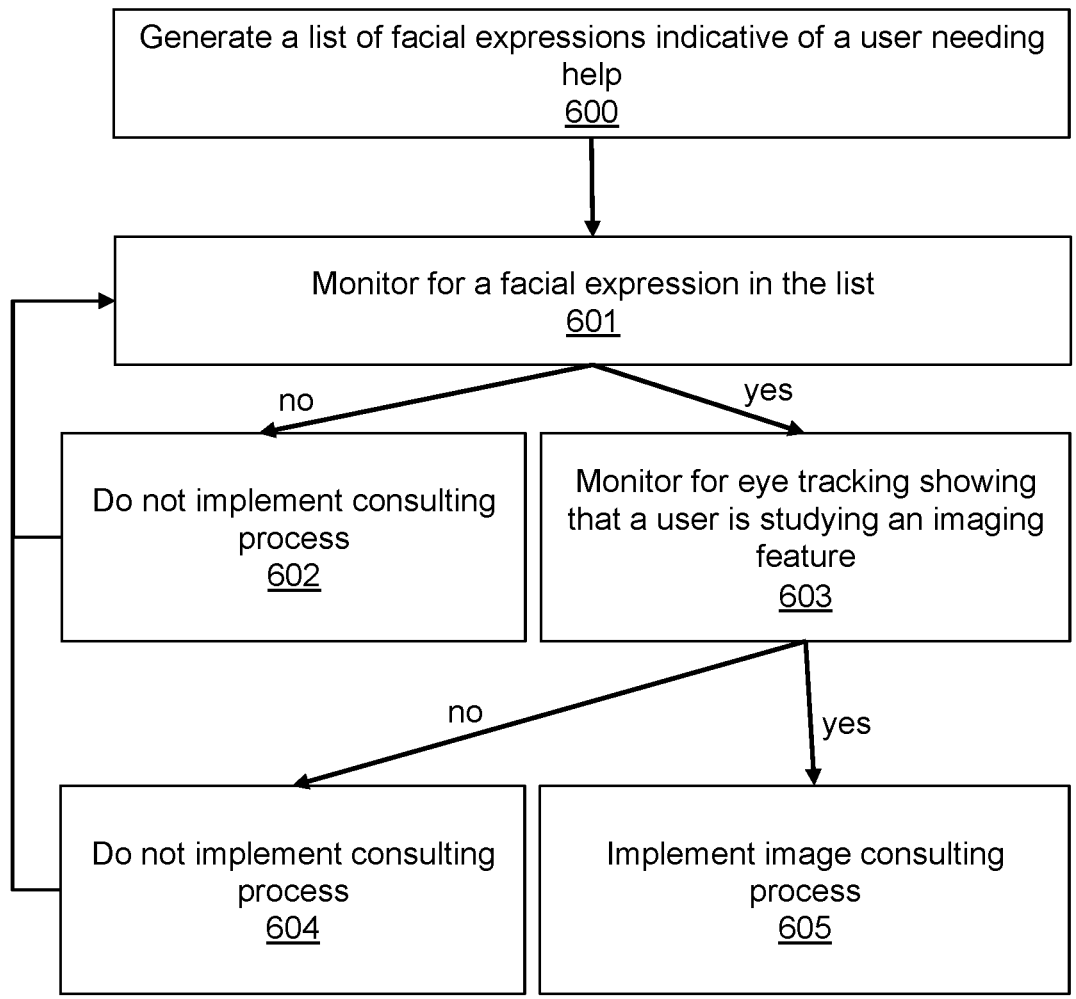
FIG. 6 illustrates when to implement the consulting process.

FIG. 6 illustrates when to implement the consulting process. 600 illustrates a processing block of generating a list of facial expressions indicative of a first user needing help with an image. 601 illustrates a processing block of monitoring for a facial expressions in the list. 602 illustrates a processing block which occurs when no facial expression is identified and wherein the consulting process is not implemented and wherein processing block 601 of monitoring for a facial expression in the list continues. 603 illustrates a processing block of monitoring for eye tracking findings showing that a user is studying an imaging feature which occurs if there is a facial expression on the list. 604 illustrates a processing block which occurs when there is no indication that the user is studying an imaging feature and wherein the consulting process is not implemented and wherein processing block 101 of monitoring for a facial expression in the list continues. 605 illustrates a processing block of implementing the image consulting process, which occurs if there is both a facial expression indication of needing help and an eye tracking indication that a user is studying an imaging feature.

Figure 7A:
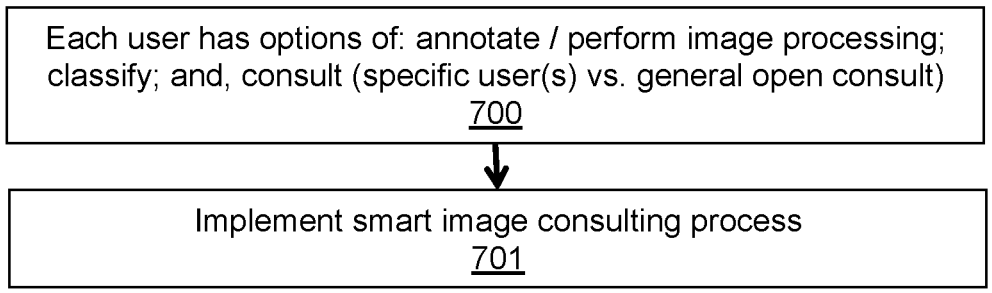
FIG. 7A illustrates a multi-mark up, multi-consultant process.

FIG. 7A illustrates a multi-mark up, multi-consultant process. Processing block 700 illustrates providing, for each user, the options to: annotate/perform image processing; classify; and, consult (specific user(s) vs. general open consult). Processing block 701 illustrates performing the smart image consulting process, as described in FIG. 5.

Figure 7B:
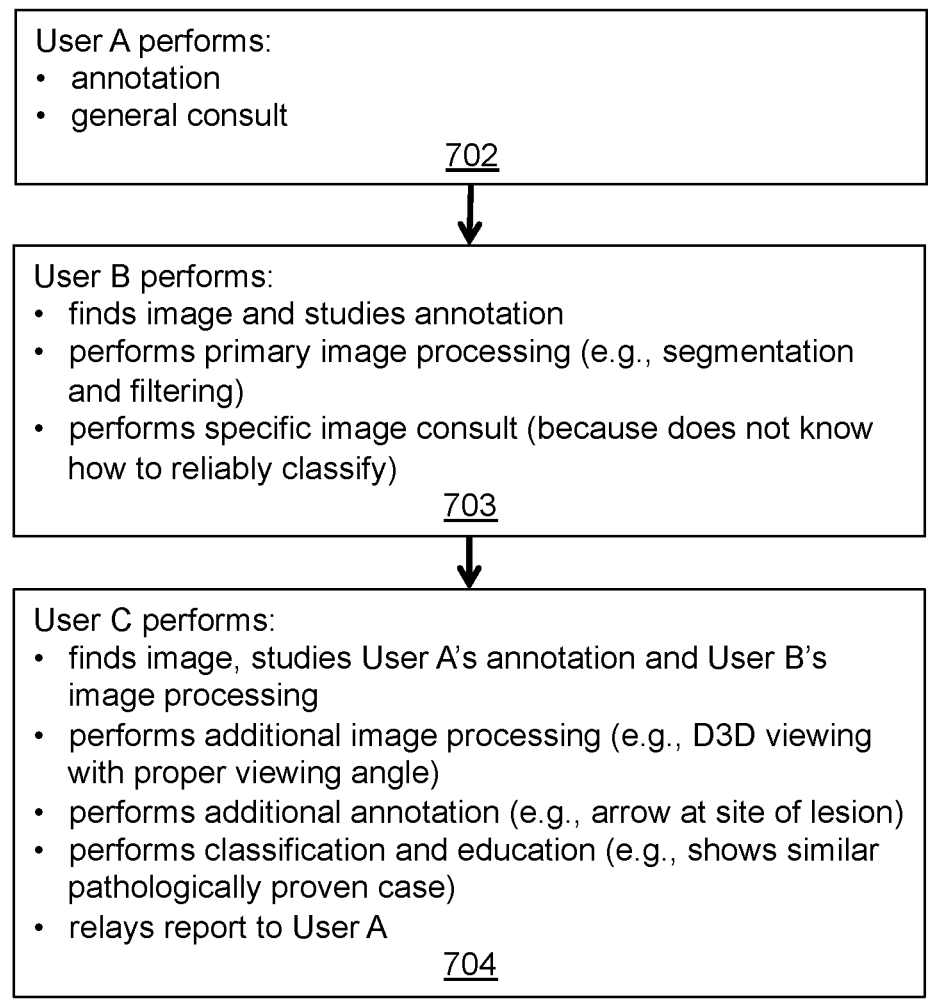
FIG. 7B illustrates an example of the multi-mark up, multi-consultant process.

FIG. 7B illustrates an example of the multi-mark up, multi-consultant process. 702 illustrates user A performing annotation(s) of the image and then a general consult. 703 illustrates user B finding the image and studying the annotation(s). Then User B performs some image processing steps including segmentation and filtering. Then User B studies the image. User B does not know how to reliably classify, but does know who is likely to know how to classify the image. Therefore User B performs a consult to a specific user. 704 illustrates user C finding the image, studying user A's annotation and User B's image processing and then performing additional image processing. For example, the user uses the D3D imaging system with viewing of the proper viewing angle. Then, user C performs an additional annotation of an arrow at the site of the lesion. Then, user C performs classification (i.e., gives specific imaging diagnosis). Then user C performs additional annotation (e.g., arrow at site of lesion). Then, user C performs education (e.g., shows similar pathologically proven case) and relays annotation, education, classification and classification to User A. This system is useful because large consulting networks would be possible. For example, if a local hospital performs the imaging consulting process, but no one there confidently knows the diagnosis, then the image can be sent to a larger network, and to specialty centers, such as the Armed Forced Institute of Pathology in Bethesda, Md.

Figure 8A:
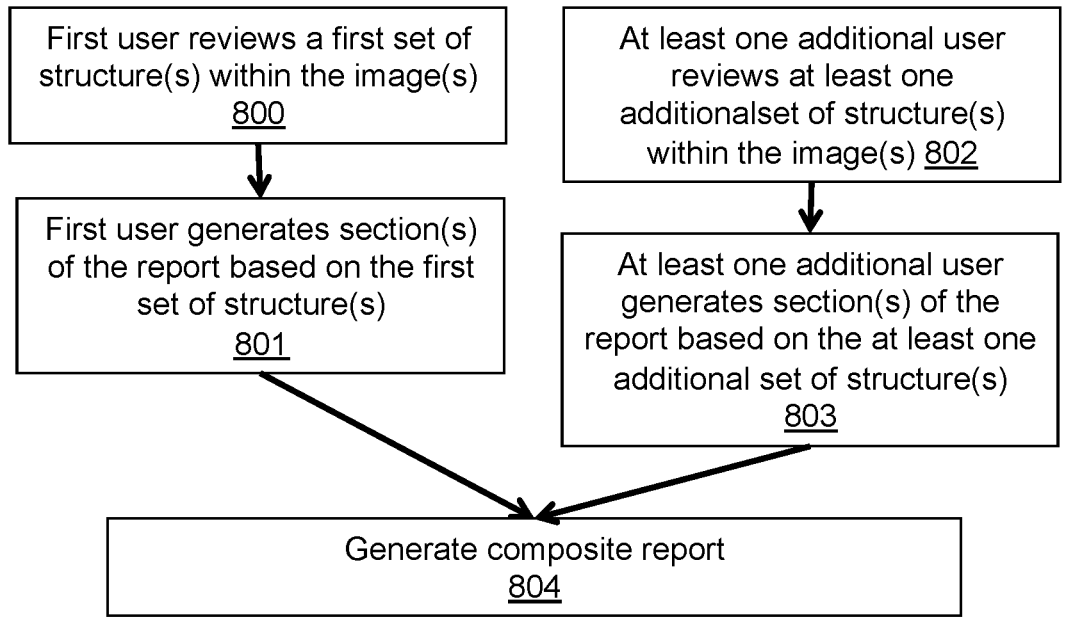
FIG. 8A illustrates a process for multi-user image analysis and reporting.

FIG. 8A illustrates a process for multi-user image analysis and reporting. The multi-user image analysis and reporting has a key role in improving outcomes in emergency situations where a large amount of data needs to be classified in rapid fashion. A good example of this is in trauma where a pan-CT scan (head to toe) is performed. The trauma surgeon needs to know the results almost immediately so they can triage the patient to the operating room for surgery or to the intensive care unit for stabilization. 800 illustrates a first user reviewing a first set of structure(s) within the image(s). 801 illustrates the first user generating section(s) of the report based on the first set of structure(s). 802 illustrates a second user reviewing a second set of structure(s) within the image(s). 803 illustrates the first user generating section(s) of the report based on the first set of structure(s). 804 illustrates generating a composite report.

Figure 8B:
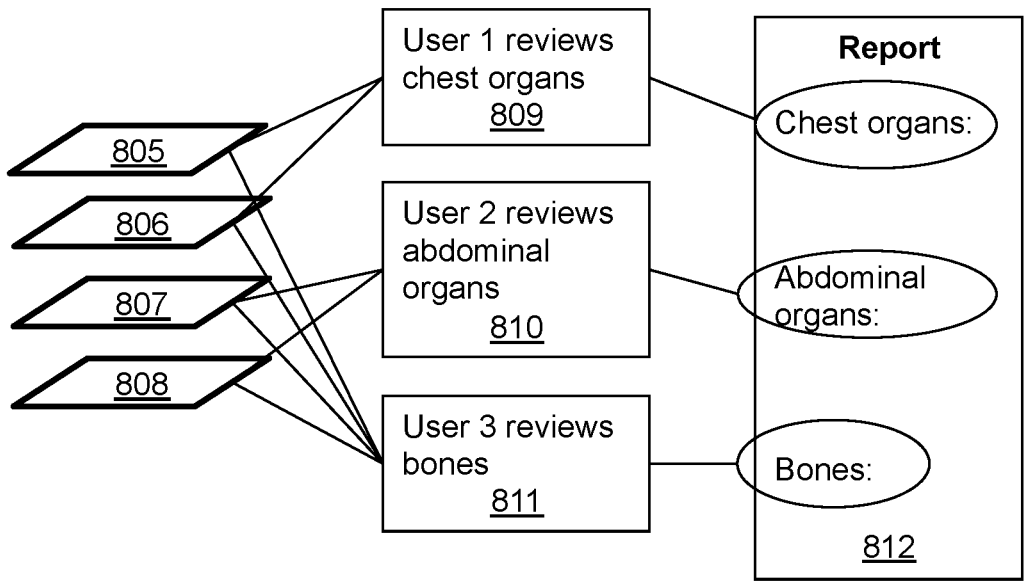
FIG. 8B illustrates an example of multi-user image analysis and reporting of a CT scan of the chest, abdomen and pelvis for performed for trauma.

FIG. 8B illustrates an example of multi-user image analysis and reporting of a CT scan of the chest, abdomen and pelvis for performed for trauma. 805 illustrates a set of CT slices containing chest organs and bones. 806 illustrates a set of CT slices containing chest organs and bones. 807 illustrates a set of CT slices containing abdominal organs and bones. 808 illustrates a set of CT slices containing abdominal organs and bones. 809 illustrates wherein user 1 reviews the chest organs on CT images 805 and 806. 810 illustrates wherein user 2 reviews the abdominal organs on CT images 807 and 808. 811 illustrates wherein user 3 reviews the bones on CT images 809 and 810. 812 illustrates the composite report, which includes a radiology template wherein the chest organs section is completed by user 1, the abdominal organs section is completed by user 2 and the bones section is completed by user 3. The sections can be filled in in real time (and viewed by the trauma surgeon) or upon radiologist approval for fastest delivery of care. In some embodiments, the user can co-sign portions of the report. These portions can be marked up accordingly.

FIG. 9 illustrates examples of image viewing strategies during the multi-mark up, multi-consultant process. To optimize viewing, the user can modify the 3D dataset based on a variety of conventional viewing strategies, such as modifying the visual representation, such as changing the color and transparency, filtering, etc. Additionally, the user can utilize user drawn shapes, arrow(s), 3D cursor(s) and segmentation strategies. In addition, the user can modify the virtual object through a range of advanced viewing strategies. This user can implement a double windowing technique via U.S. Pat. No. 10,586,400, PROCESSING 3D MEDICAL IMAGES TO ENHANCE VISUALIZATION, which is incorporated by reference in its entirety. The user can implement an interaction of 3D dataset with geo-registered tools, as described in U.S. Pat. No. 10,712,837, USING GEO-REGISTERED TOOLS TO MANIPULATE THREE-DIMENSIONAL MEDICAL IMAGES, which is incorporated by reference in its entirety. Examples of geo-registered tools include, but are not limited to the following: knife; scissors; platform; forceps; staples; and, a wide range of other types of surgical tools. The user can perform interaction of 3D dataset with virtual tools, as described in PCT/US19/47891, A VIRTUAL TOOL KIT FOR 3D IMAGING, which is incorporated by reference in its entirety. The user can perform "ghost imaging" per U.S. patent application Ser. No. 16/010,925, INTERACTIVE PLACEMENT OF A 3D DIGITAL REPRESENTATION OF A SURGICAL DEVICE OR ANATOMIC FEATURE INTO A 3D RADIOLOGIC IMAGE FOR PRE-OPERATIVE PLANNING, which is incorporated by reference in its entirety. The user can insert flow visualization features, as described in U.S. patent application Ser. No. 16/506,073, A METHOD FOR ILLUSTRATING DIRECTION OF BLOOD FLOW VIA POINTERS, and Ser. No. 16/779,658, 3D IMAGING OF VIRTUAL FLUIDS AND VIRTUAL SOUNDS, which are incorporated by reference in their entirety. The user can perform voxel manipulation strategies, per U.S. patent application Ser. No. 16/195,251, INTERACTIVE VOXEL MANIPULATION IN VOLUMETRIC MEDICAL IMAGING FOR VIRTUAL MOTION, DEFORMABLE TISSUE, AND VIRTUAL RADIOLOGICAL DISSECTION, which is incorporated by reference in its entirety.

FIG. 10 illustrates criteria that an algorithm can use to find the most appropriate consult. First, whether or not a user is actively analyzing a user's current work load (e.g., to prevent from disturbing). Next, analyze past images of each user in the group. High image similarity can be an indication for presenting the image to a user. For example, an artificial intelligence algorithm can analyze a user's prior images that he/she has reported on. If one of them is extremely similar to an image from a first user, then that can be an indication for determining consultant. Next, analyze past reports of each user in the group. High report similarity can be an indication for presenting the image to a user. Next, analyze past consult patterns. Those that were proven to be successful in the past can be used to guide future consultation patterns. For example, feedback from past consult patterns (e.g., satisfaction scores) can be logged and used to determine future consultant patterns. Next, is urgency of the case. If a case is urgent, then this can be a factor in determining consultant patterns. Next, is to determine whether or not user's should be excluded from consulting. For example, a user can turn off a "availability for consulting" button. Next, is to determine which user(s) are available.

FIG. 11A illustrates features of a first user who needs help with a neuroradiology imaging examination. This example assumes a large network of radiologists. 1100 illustrates Radiologist #456 who is a general radiologist with special skill of asbestos related lung disease. Radiologist #456 needs help with a temporal bone imaging examination. As discussed in FIG. 3, factors such as a user's facial expression can be used to determine that a consultation is needed.

FIG. 11B illustrates features of a five users who have expertise in neuroradiology. 1101 illustrates Radiologist #911 who is a neuroradiologist with specialty skills of cerebral vasculitis. 1102 illustrates Radiologist #316 who is a neuroradiologist with specialty skills of PET imaging of dementia. 1103 illustrates Radiologist #200 who is a neuroradiologist with specialty skills of skull base tumors. 1104 illustrates Radiologist #415 who is a neuroradiologist with specialty skills of phacomatoses. 1105 illustrates Radiologist #899 who is a neuroradiologist with specialty skills of temporal bone lesions.

FIG. 11C illustrates the connection of the first user with the optimum consultant. Note that the smart image consulting process, as described in FIG. 5, is performed. As a result, the optimum consultant can receive a consulting RVU.

FIG. 12 illustrates a modified relative value unit (RVU) system based on factors other than just type of imaging examination. Some imaging examinations are normal and a radiologist has little question in the diagnosis. The radiologist quickly reviews and signs a normal report. Some imaging examinations, however, are abnormal and a radiologist has many questions about the image. So much so that a consulting process occurs. When this is the case, the radiologist may unproductive that hour. Furthermore, the radiologist who performs the consultation would also appear unproductive that hour. Therefore, in this situation, an imaging examination is assigned modified RVU. A modified RVU can be modified based on an imaging examination's pathology or lack thereof. For example, if a user reads a normal chest x-ray, the assigned RVU can be a value of 0.1. However, if a user reads an abnormal chest x-ray (contains lung cancer), then the assigned RVU can be at a higher value of 0.2. This system would be useful to better monitor productivity in a fair manner. Other factors can also be used to compute a RVU. For example, an aspect of patient history can be used. For example, indication of the study of a "20 foot fall" can be used to computer a modified RVU. Another such factor is laboratory examination. For example, a user with a WBC count of 20 can be given a higher modified RVU for an imaging examination. Another factor in determining the RVU are factors related to a consulting process (e.g., number of consultations, time involved during consultation). In the broadest sense, an RVU is currently based on only the type of imaging examination. In this patent, a modified RVU score can be utilized based on at least one additional factor. This modified RVU system is important because it can more fairly assess productivity amongst radiologists. The number of examinations, number of consultations, and number of referrals to consultant (i.e., by $3^{rd}$ user) can be used to determine productivity.

FIG. 13 illustrates a worklist for radiologists. The first column illustrates a list of unread examinations. For example, these can be a set of images that are recently acquired by the technologists and have never been opened by any radiologist. A radiologist who interprets and examination and files a report would receive an RVU or modified RVU per FIG. 12. The second column illustrates a list of general (open to anyone) cases needing consultation. For example, Dr. J, a radiologist, may be confused on how to measure a scoliosis film and therefore performs annotations on the image and sends it to the general consultation list. Dr. K, a radiologist, sees the image pop up, knows how to perform the measurement, performs the consultation to Dr. J. For the consulting process to work optimally (and fairly), Dr. K would receive some RVU or the like. The third column illustrates a list of general (only seen by you) cases needing consultation. Assume that this list is seen by Dr. W. A case sent only to Dr. W would be shown in this third column. A case sent from Dr. J to Dr. K would not be seen in Dr. W's third column. In some cases, Dr. W may see the case, not know what it is, and then kick it back to the second column (general pool) where any radiologist can review the case. Dr. W could, as previously discussed, also pass the annotated image (e.g., visible boundary) into the general pool. Additionally, the number of times a case is passed can be used in the analysis (e.g., of a modified RVU).

FIG. 14 illustrates using artificial intelligence to determine an optimum reference image. 1400 illustrates determining structure(s) (e.g., bones) of interest or area of interest in a first imaging examination (e.g., a patient's cross-sectional medical imaging examination comprises at least one of a computed tomography (CT) scan, a magnetic resonance imaging (MRI) examination, a positron emission tomography (PET) scan, a single photon emission computed tomography (SPECT) scan and an ultrasound examination). Note that the preferred embodiment for "determining" is via user selection. Another novel method that can be incorporated in this technique includes wherein an AI algorithm classifies a structure as abnormal. Once this occurs, the AI algorithm selects the structure which it classifies as abnormal and then implements the process to identify the closest matched cross-sectional imaging examination. In some embodiments, the cross-sectional imaging examination can be presented in the form of slices. In some embodiments, the cross-sectional imaging examination can be presented in the form of a volume rendered image. In some embodiments, the structure from which the optimized reference image is desired can be selected by a user. For example, assume the user is scrolling through image slices. Assume that the user stops at axial image slice 91. Assume that this image slice includes the cochlea, the vestibule, the facial nerve canal, the internal auditory canal, the brainstem, the cerebellum and the orbit. Assume that at this image, the user wants to select the optimum reference image for the cochlea. One option is for the user to perform segmentation of the item of interest (e.g., cochlea). The algorithm can then aim to find the closest match for the segmented structure within a particular slice. In some embodiments, however, the optimum reference image can be performed for the slice as a whole or combination of multiple segmented structures. In other words, in some embodiments, the structure of interest can be a single anatomic structure (e.g., a cochlea bone within the middle ear). In some embodiments, the structures of interest can be numerous anatomic structures (e.g., all bones, all ligaments, all tendons of a joint). Other embodiments include wherein the structure of interest comprises: an anatomic finding; a pathologic finding; a surgical device; a medical device; an imaging artifact; a foreign body; and, a feature identified as abnormal on a prior imaging examination (e.g., past imaging examination which showed an abnormality is labeled on today's examination); and, an imaging feature known to be poorly understood by a user. Note that a key step to optimize the identification of an optimized reference image from a database is the performance of segmentation to delineate the boundary of the structure of interest. 1401 illustrates analyzing (using artificial intelligence) a database of images to determine a second imaging examination from a database of imaging examinations (e.g., archive of labeled imaging datasets, archive of unlabeled imaging datasets) which is a close (or closest) match to the structure of interest or area of interest in the first imaging examination. 1402 illustrates presenting the close (or closest) match to a user. A first presentation option is to present the image from the equivalent volume rendered appearance. Specifically, a volume rendered image of the second imaging examination can be presented to match the first imaging examination. This would require a matched filtering algorithm wherein the current cross-sectional imaging examination of interest is set to match a reference cross-sectional imaging examination. Filtering techniques are discussed in U.S. Pat. No. 8,384, 771. Next, this would require a matched viewing angle wherein the viewing angle of the current cross-sectional imaging examination matches that of the reference cross-sectional imaging examination. Next, this would require a matched viewing distance wherein the viewing distance of the current cross-sectional imaging examination matches that of the reference cross-sectional imaging examination. Note that the image could be presented in accordance with ghosting presentation technique per U.S. Pat. No. 10,864,043 if so desired. Next, present the image from the equivalent slice. Specifically, the algorithm will cause the second imaging examination to be reconstructed to match the first imaging examination in all ways possible. For example, the slice thickness, window width, window level, and all other viewing parameters of the current cross-sectional imaging examination would be applied to the reference imaging examination as determined by the AI algorithm. Thus, this technique not only matches the images, it also processes the reference imaging examination so that it matches that of the current imaging examination of interest. In some embodiments, however, the current imaging examination can be processed to appear similar to the reference image. Note that it is the preferred embodiment to match the current imaging examination and the reference imaging examination based on the raw data (e.g., the Houndsfield units for a segmented structure), not on a post-processed image (e.g., an image that has already been windowed and leveled). This improves the ability to accurately achieve an image match. Thus, a point of novelty is not only the identification of a closest (or close) match, but it is the ability to process either the reference cross-sectional imaging examination or the current cross-sectional imaging examination so that they are presented in a similar fashion. This improves a user's ability to visually analyze the current cross-sectional imaging examination. In some embodiments, the image can be matched by using the same grayscale appearance. Namely, process the matched imaging examination to have the same window width and window level setting to match the first imaging examination. Analysis options include: user review of a report from the second image to see what the past radiologist said about the structure of interest/area of interest. In some embodiments, the matched imaging examination is presented in a superimposed fashion on the current imaging examination. In some embodiments, the matched imaging examination is presented adjacent to the current imaging examination. This is an additional improvement because it can be used for continuous improvement for either or both the radiologist who is interpreting the current imaging examination or the radiologist who interpreted the matched cross-sectional imaging examination. Note that this technique is most useful for cross-sectional imaging examinations because these are the most challenging to interpret; however, could also be applied to plain film or planar scintigraphy examinations. In some embodiments, however, these techniques could be applied to a wide range of other non-medical fields which rely on imaging analysis, which include, but are not limited to the following. In some embodiments, these techniques could be performed with the smart image consult process taught in this patent.

FIG. 15 illustrates using artificial intelligence to perform anatomic labeling of a patient's examination. 1500 illustrates determining an unlabeled structure of interest (e.g., large blood vessel in the abdomen) for an image (e.g., slice, volume rendered image) for a patient. Note that the preferred embodiment for "determining" is via user selection. A user can perform selection by moving a mouse to the structure of interest. Other types of interactions are also possible, which include hand gestures, joystick inputs or keyboard inputs. Additionally, selection can be performed via eye tracking, which is described in U.S. patent application Ser. Nos. 16/936,293 and 16/842,631, which are incorporated by reference in its entirety. Another novel method that can be incorporated in this technique includes wherein the "determining" is performed by an AI algorithm classifies a structure as abnormal. For example, normal structures can be selected to not be labeled. Abnormal structures can be selected to be labeled. This novel selective labeling technique improves upon the prior art by helping to not only communicate the abnormality, but to also label it, which would help radiologists improve their understanding of complex anatomic features. This is particularly important as spatial resolution and contrast resolution improves and the number of structures increases (e.g., the cranial nerve nuclei in the brainstem, which are poorly understood even by experienced neuroradiologists). Neuroradiologists will improve their knowledge even during diagnostic work. Once this occurs, the AI algorithm selects the structure which it classifies as abnormal and then implements the process to identify the closest matched cross-sectional imaging examination. Another embodiments includes performing the selection of which structures to label based on an artificial intelligence analysis of the patient history, patient demographics or via language in a radiologist's report. Note that these techniques of AI analysis of patient history, patient demographics and radiologist's report are further taught in U.S. patent application Ser. No. 16/597,910, which is incorporated by reference in its entirety. Note that the preferred embodiment is utilization of an image is from a cross-sectional medical imaging examination (computed tomography (CT) scan, a magnetic resonance imaging (MRI) examination, a positron emission tomography (PET) scan, a single photon emission computed tomography (SPECT) scan and an ultrasound examination). Note that a segmentation process can be used to delineate the boundary of the structure of interest selected (e.g., by the user). 1501 illustrates analyzing (using artificial intelligence) a database of images (wherein the images are labeled) to determine a label (e.g., "aorta") for the structure of interest. Note that the label will be a text label for the structure. 1502 illustrates presenting the label (e.g., "aorta") for said structure to a user via a visual text notification, which is the preferred embodiment. Auditory notifications could also be performed, if so desired. Preferred label has line extending over areas of image of non-interest. Areas of non-interest can be determined by: a user; an AI algorithm analyzing the images, the patient history and reasons for the examination, the patient demographics; shortest length of line connecting label to structure; or combination thereof. Note that the structure can be an anatomic finding or a pathologic finding or a device (medical device or surgical device or an artifact). 1503 illustrates presenting a location indicator to communicate to a user the precise spot of the label on the image comprising. A first technique includes presenting a digital object (e.g., red dot) at the finding (anatomic or pathologic finding) on the image to correspond to the label. A second technique includes a cursor (e.g., directed by a user such as via a mouse movement or via a computer algorithm) hovering over structure of interest and the label is displayed on a monitor. A third technique is a using a line to connect structure of interest to label. Note that the line can be positioned so as not to cover other structures of interest. A range of structures can be labeled, which include: bone(s); artery(ies); vein(s); ligament(s); tendon(s); nervous system structure(s); cardiovascular structure(s); gastrointestinal structure(s); pulmonary structure(s); endocrine system structure(s); genitourinary structure(s); muscle(s); orbital structure(s); inner ear structure(s); lymphatic structure(s); surgical hardware such as an interbody spacer for spine surgery and, medical device(s), such as a port-a-cath or an NG tube. Some embodiments comprise wherein a user is alerted to the label by an auditory notification. 1504 illustrates an option retrain the AI algorithm by: a user adjusts the location indicator; and, a user adjusts the segmentation algorithm (e.g., delineation of the structure is re-defined).

What is claimed is:

1. A method comprising:
   determining at least one unlabeled structure within a cross-sectional medical imaging examination
      wherein said at least one unlabeled structure comprises imaging feature(s) within said cross-sectional medical imaging examination,
      wherein said at least one unlabeled structures comprises an anatomic finding,
      wherein said at least one unlabeled structure does not have an associated text label(s), and
      wherein said cross-sectional medical imaging examination comprises at least one of a computed tomography (CT) scan, a magnetic resonance imaging (MRI) examination, a positron emission tomography (PET) scan, a single photon emission computed tomography (SPECT) scan and an ultrasound examination;
   performing an analysis of said at least one unlabeled structure
      wherein said analysis comprises an artificial intelligence (AI) algorithm,
      wherein said analysis determines a text label for each unlabeled structure of said at least one unlabeled structure to cause said at least one unlabeled structure to become at least one labeled structure; and
   presenting a labeled cross-sectional imaging examination to a user wherein said labeled cross-sectional imaging examination contains said at least one labeled structure.

2. The method of claim 1 further comprising wherein said determining said at least one unlabeled structure is based on selection by said user.

3. The method of claim 1 further comprising wherein said determining said at least one unlabeled structure is based on a second AI algorithm.

4. The method of claim 1 further comprising wherein an optimized reference image is presented adjacent to said labeled cross-sectional imaging examination.

5. The method of claim 1 further comprising wherein an optimized reference image is presented superimposed on said labeled cross-sectional imaging examination.

6. The method of claim 1 further comprising wherein said at least one unlabeled structures comprises a pathologic finding.

7. The method of claim 1 further comprising wherein said at least one unlabeled structures comprises a surgical device.

8. The method of claim 1 further comprising wherein said at least one unlabeled structures comprises a medical device.

9. The method of claim 1 further comprising wherein said at least one unlabeled structures comprises an artifact.

10. The method of claim 1 further comprising wherein said at least one unlabeled structures comprises a foreign body.

11. The method of claim 1 further comprising wherein said at least one unlabeled structures comprises a feature identified as abnormal on a prior imaging examination.

12. The method of claim 1 further comprising wherein said at least one unlabeled structures comprises an imaging feature known to be poorly understood by said user.

13. The method of claim 1 further comprising presenting a location indicator at the at least one labeled structure to communicate to said user the precise spot of the label on the image.

14. The method of claim 13 further comprising wherein said location indicator comprises a digital object placed at the site of the at least one labeled structure.

15. The method of claim 13 further comprising:
   wherein said location indicator comprises a cursor hovering over structure of interest, and
   wherein said label is displayed on a monitor.

16. The method of claim 13 further comprising wherein said location indicator is a line to connect said at least one labeled structure of interest to a label.

17. The method of claim 1 further comprising wherein said determining at least one unlabeled structure within a cross-sectional medical imaging examination is based on eye tracking of said user.

18. A method comprising:
   presenting at least one unlabeled structure within a cross-sectional medical imaging examination
      wherein said at least one unlabeled structure is selected by a first artificial intelligence (AI) algorithm,
      wherein said first AI algorithm classifies said structure as abnormal,
      wherein said at least one unlabeled structure comprises imaging feature(s) within said cross-sectional medical imaging examination,
      wherein said at least one unlabeled structure does not have an associated text label(s), and
      wherein said cross-sectional medical imaging examination comprises at least one of a computed tomography (CT) scan, a magnetic resonance imaging (MRI) examination, a positron emission tomography (PET) scan, a single photon emission computed tomography (SPECT) scan and an ultrasound examination;
   performing an analysis of said at least one unlabeled structure
      wherein said analysis comprises a second AI algorithm,
      wherein said analysis assigns a text label for each unlabeled structure of said at least one unlabeled structure to cause said at least one unlabeled structure to become at least one labeled structure;
   presenting a labeled cross-sectional imaging examination to a user wherein said labeled cross-sectional imaging examination contains said at least one labeled structure; and
   presenting a location indicator at the at least one labeled structure to communicate to said user a precise spot of a label on an image wherein said location indicator comprises a line connecting said at least one labeled structure to said label.

19. A method comprising:
   loading a cross-sectional medical imaging examination into an image processing system
      wherein at least one unlabeled structure comprises imaging feature(s) within said cross-sectional medical imaging examination,
      wherein said at least one unlabeled structure within said cross-sectional medical imaging examination is determined based on eye tracking of a user,
      wherein said at least one unlabeled structure does not have an associated text label(s), and wherein said cross-sectional medical imaging examination comprises at least one of a computed tomography (CT) scan, a magnetic resonance imaging (MRI) examination, a positron emission tomography (PET) scan, a single photon emission computed tomography (SPECT) scan and an ultrasound examination;

performing an analysis of said at least one unlabeled structure by said image processing system
wherein said analysis comprises artificial intelligence,
wherein said analysis assigns a text label for each unlabeled structure of said at least one unlabeled structure to cause said at least one unlabeled structure to become at least one labeled structure;

presenting a labeled cross-sectional imaging examination wherein said labeled cross-sectional imaging examination contains said at least one labeled structure.

\* \* \* \* \*